United States Patent [19]

Wiksell

[11] Patent Number: 5,062,827
[45] Date of Patent: * Nov. 5, 1991

[54] DEVICE IN ULTRASONIC ASPIRATORS

[75] Inventor: Hans Wiksell, Täby, Sweden

[73] Assignee: Swedemede AB, Uppsala, Sweden

[*] Notice: The portion of the term of this patent subsequent to Dec. 12, 2006 has been disclaimed.

[21] Appl. No.: 309,936

[22] Filed: Feb. 14, 1989

Related U.S. Application Data

[63] Continuation of Ser. No. 927,185, Nov. 5, 1986, abandoned.

[30] Foreign Application Priority Data

Nov. 8, 1985 [SE] Sweden ............................ 8505289

[51] Int. Cl.$^5$ .......................................... A61B 17/36
[52] U.S. Cl. ............................ 604/22; 128/240 AA
[58] Field of Search ............... 128/24 A, 305; 604/22; 310/316

[56] References Cited

U.S. PATENT DOCUMENTS

| | | | |
|---|---|---|---|
| 2,514,080 | 7/1950 | Mason et al. | 128/24 A |
| 2,748,298 | 5/1956 | Calosi et al. | 128/24 A |
| 3,447,051 | 5/1969 | Attwood et al. | 310/316 |
| 3,862,630 | 1/1975 | Balamuth | 128/24 A |
| 4,271,371 | 6/1981 | Furuichi et al. | 310/316 |
| 4,371,816 | 2/1983 | Weiser | 310/316 |
| 4,425,115 | 1/1984 | Wuchinich | 604/22 |
| 4,445,063 | 4/1984 | Smith | 310/316 |
| 4,468,581 | 8/1984 | Okada et al. | 310/316 |
| 4,493,694 | 1/1985 | Wuchinich | 604/22 |
| 4,516,398 | 5/1985 | Wuchinich | 604/22 |
| 4,587,958 | 5/1986 | Noguchi et al. | 128/24 A |
| 4,886,060 | 12/1989 | Wiksell | 604/22 |

OTHER PUBLICATIONS

Frederick, Julian R., Ultrasonic Engineering, 1965, pp. 1-130.
Eisner et al., A Longitudinally Resonant Stub for Vibrations of Large Amplitude, Ultrasonics, Apr.-Jun. 1965, pp. 88-98.

Primary Examiner—Lee S. Cohen
Assistant Examiner—John P. Lacyk
Attorney, Agent, or Firm—Armstrong, Nikaido, Marmelstein, Kubovcik & Murray

[57] ABSTRACT

Device in ultrasonic knives of the kind including a transducer for converting electrical energy at ultrasonic frequency to a mechanical oscillation. An amplitude transformer (2) forms the tip of the knife. The length of the ultrasonic transformer is in the order of magnitude 0.72 times the wavelength of the ultrasonic frequency. The ultrasonic transformer is an integral unit comprising a cylindrical portion (40), an integral portion (41) which is the curve of a wave function of the fourth order Fourier form, and a tip portion (42) which is conical, whereby the maximum stroke of the longitudinal oscillation mode of the knife is a desired resonance frequency, this resonance frequency being greatly separated, in the order of magnitude 20% with relation to the resonance frequency, from resonance frequency pertaining to harmonics of the desired resonance frequency in the longitudinal oscillation mode, and resonance frequency pertaining to oscillations in the transverse mode.

7 Claims, 2 Drawing Sheets

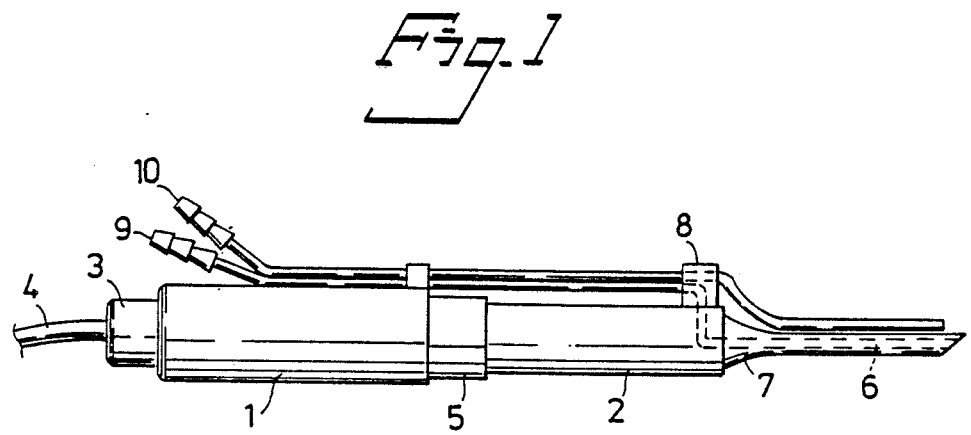
Fig. 1
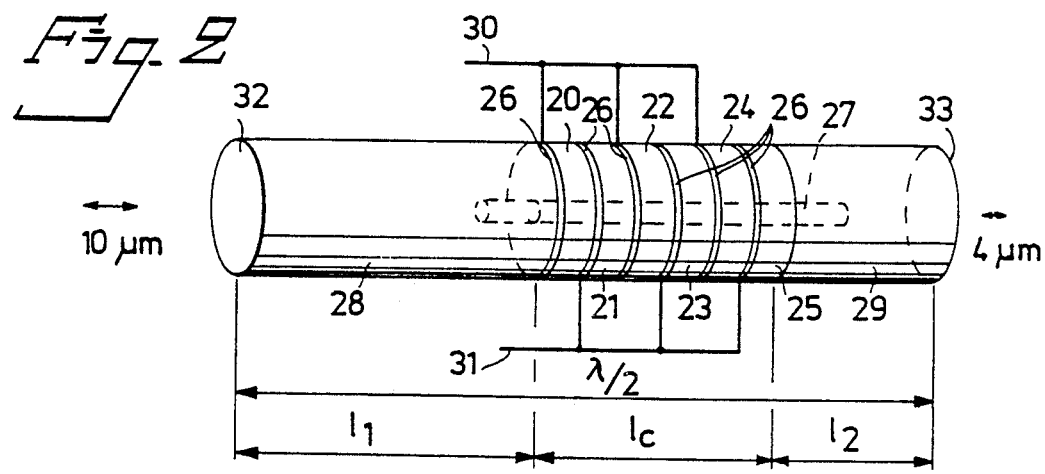
Fig. 2
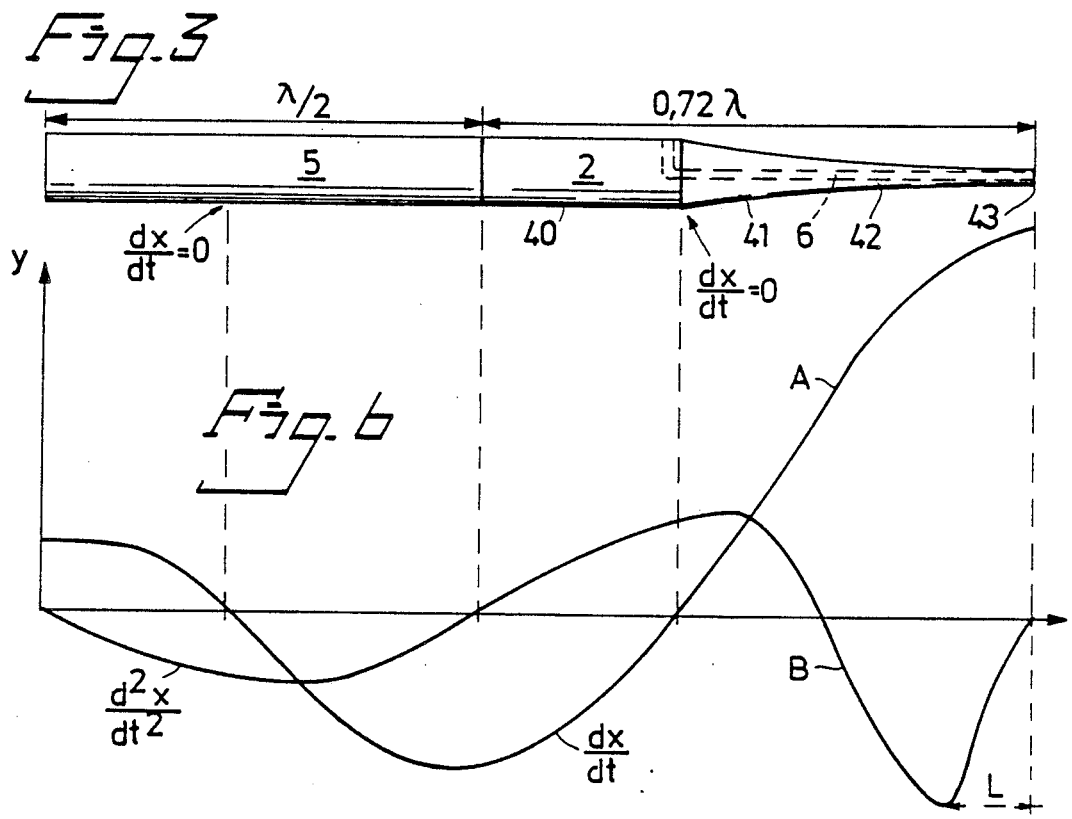
Fig. 3
Fig. 6

DEVICE IN ULTRASONIC ASPIRATORS

This application is a continuation of application Ser. No. 927,185 filed Nov. 5, 1986, now abandoned.

BACKGROUND OF THE INVENTION

The present invention relates in general to ultrasonic aspirators and in particular to an ultrasonic aspirator intended for use in surgical operations for removing tissue. More specifically, the ultrasonic aspirator is of the kind including an integrally implemented amplitude transformer with a tip intended to be brought into contact with the tissue, and to serve as a kind of knife with the ability to remove tissue with precision, the tissue being comminuted by the ultrasonic effect into fragments which are sucked away, aspirated, through the elongate tip portion of the ultrasonic aspirator, this portion being the one providing the removal mentioned. Somewhat improperly the ultrasonic aspirator is hereinafter called an ultrasonic knife. A transducer working as a vibrator is mechanically connected to the amplitude transformer and causes the tip portion to oscillate longitudinally. A frequency generator feeds electrical energy of ultrasonic frequency to the transducer unit, which converts this energy into a mechanical longitudinal oscillation, the amplitude of which is reinforced by the amplitude transformer so that the tip portion executes the longitudinal oscillation with great oscillation amplitude.

Ultrasonic knives of the kind mentioned above are known from such as U.S. Pat. Nos. 3,526,219, 4,063,557, 4,223,676, 4,525,115 and EP-A- 0 139 753.

In order that an ultrasonic knife shall function clinically satisfactorily it is an absolute requirement that the tip portion executes a pure longitudinal oscillation movement. Oscillation in the transverse direction must not occur, since such movement would be directly destructive for operations in sensitive areas. Every oscillating mass, and particularly a complicated ultrasonic transducer, has a plurality of resonance frequencies at which oscillation amplitudes in the transverse and/or longitudinal direction are possible. The resonance frequencies change when the resonance conditions of the oscillating body are modified, e.g. when it is immersed in water or comes into contact with tissue. What is particularly important for an ultrasonic knife is that when the knife is in operation, and thereby changes its resonance frequency, the frequency generator must change the frequency of the electrical energy supplied to the knife so that the knife continues to oscillate and thereby to remove material. It is known to use frequency control circuits for this purpose, and voltage controlled oscillators in particular. It is then important that the voltage controlled oscillator locks on to the resonance frequency pertaining to the longitudinal oscillation of the ultrasonic converter and not to its harmonics, and neither to any other resonance frequency pertaining to transverse oscillations. The undesired resonance frequencies are denoted spurious frequencies below. Depending on the ultrasonic transformer geometry, the resonance frequencies, including the spurious resonance frequencies, may be close to each other with regard to frequency, and different means have therefore been used to ensure that the voltage controlled oscillator really locks on to the desired resonance frequency. Accordingly, there is described in the U.S. Pat. No. 4,275,363 a frequency sweeping means which first sweeps a frequency generator over a wide frequency range before the knife is allowed to start, this range being much wider than the one covered by the frequency-following oscillator used, thus to determine the frequency at which the desired resonance (longitudinal oscillation at greatest amplitude) occurs and thereafter to adjust the frequency generator such that the oscillator locks on to this desired frequency. Apart from a voltage controlled oscillator the means includes a resonance point detector, sweeping circuits, phase detectors, flipflops, memory etc. After the desired frequency has been set, the knife may be used for cutting. U.S. Pat. No. 4,223,767 shows a frequency control circuit where a fixed filter has transmission properties such that it only transmits frequency control signals corresponding to a frequency close to the desired resonance frequency.

Two control loops, one for frequency control and the other for amplitude control, are used. The stroke of the knife tip is used as control variable. The total impedance of the resonating system actuates the phase shift of an amplifier and controls the frequency in the frequency control loop. In this patent the physical length of the amplitude transformer is half the wave length of the desired resonance frequency.

The present invention has the object of achieving a simplified frequency control circuit which automatically follows the resonance frequency alterations of the knife and securely locks the frequency generator oscillator on to the desired resonance frequency (longitudinal oscillation with intended amplitude). The electric circuit used here must function securely, have a simple construction, simple tuning and be able to produced using standard components. This is achieved in accordance with the invention in that the amplitude transformer is given definite geometric forms, which are described in detail below, resulting in that the spurious resonance frequencies are greatly separated with respect to frequency from the desired resonance frequency. With reference to the desired resonance frequency the frequency separation is in the order of magnitude of about 20%. In this way, a simple conventional oscillator with a narrow adjustment range can be used without risk of the oscillator locking on to incorrect frequencies. The phase angle between current and voltage of the electrical energy supplied to the knife is used as control variable.

The mentioned geometrical form in accordance with the invention of the ultrasonic transformer furthermore results in the advantage that the ultrasonic knife may be used repeatedly without needing to be exchanged after each operation, as is the case with the knife according to the U.S. Pat. No. 4,223,676, for example. The inventive ultrasonic knife will thus be cheap in operation. In addition, it may be sterilized by autoclaving, which is an advantage over the knife according to the U.S. patent just mentioned, which must be sterilized in the presence of ethylene oxide gas. The ultrasonic knife in accordance with the invention can sustain the high autoclave temperature due to the material selected for the amplitude transformer and the transducer and due to the prestressing of the transducer as described further below and will not disintegrate.

The geometrical form in accordance with the invention also entails that problems relating to so called parametric pumping are reduced. In short parametric pumping means that non-linear phenomenons appearing in the material structure, especially in a resonance body which is excited by energies of a spectrum of different frequencies which are generated, due to cavitation phenomenons, will develop a number of non-desired resonances in the resonance body.

In accordance with the invention the amplitude transformer shall have a length in the order of magnitude 0.72 times the wave length of the desired resonance frequency. In addition, taken from the connection to the transducer and to the tip of the knife, it shall be made in a single unit comprising three sections, namely a cylindrical section nearest the transducer, followed by a section the geometry of which that of a wave function of the fourth order Fourier form and an outmost, substantially conical tip portion. This geometry gives a very well-defined longitudinal oscillating movement for the tip portion simultaneously as the mechanical stresses on the tip are distributed along a portion of the tip length, this portion being a distance inwards of the tip. The life of the knife is thus increased substantially.

The geometrical form of the amplitude transformer is intermediately between an exponential function and a wave function of the fourth order Fourier form.

The invention will now be described in detail with reference to the accompanying drawings, on which

BRIEF DESCRIPTION OF THE DRAWINGS

FIG. 1 is a side view of the ultrasonic knife in accordance with the invention,

FIG. 2 illustrates the transducer,

FIG. 3 illustrates the amplitude transformer also serving as knife,

FIG. 6 is a diagram illustrating stress and amplitude distribution along the amplitude transformer of FIG. 3.

DESCRIPTION OF THE PREFERRED EMBODIMENTS

Figure 4:
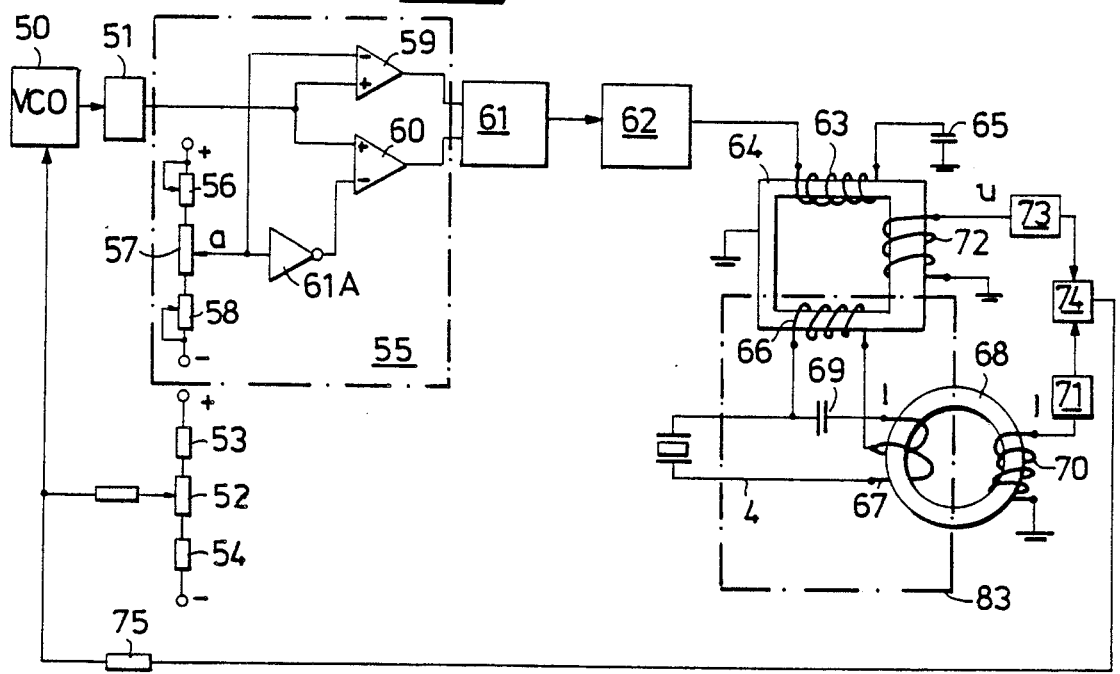
FIG. 4 is a block diagram of the equipment for supplying electricity to the ultrasonic knife.

The inventive ultrasonic knife includes a handle 1, a knife 2, a connector 3 for a two-wire cord 4 supplying alternating voltage at ultrasonic frequency to a transducer 5, to which the handle 1 is attached. The transducer converts this alternating voltage to a linear oscillating movement, the amplitude of which is amplified in the knife 2, which is implemented as an amplitude transformer, the geometry of which is described in detail below. A bore 6 extends centrally through the tip 7 of the knife and is deflected radially outwards at a schematically illustrated connection 8 for an aspiration tube 9. There is also a tube 10 for supplying isotoniosaline solution to the knife tip. As mentioned in the introduction, it is important that the free end of the knife tip executes a purely longitudinal oscillating movement without any suggestion of transverse oscillation components.

The transducer in FIG. 2 includes six rings 20-25 of a sintered ceramic material (lead titanate zirconate) between which there are inserted holed discs 26 of copper-berylium alloy. The rings 20-25 and discs 26 are placed on a titanium pin 27 threaded at both ends. There is an unillustrated sheath of electrically insulating material, thrust on to the pin to serve as electrical insulation for the discs 26. Cylindrical resonance rods 28, 29 made from the magnesium alloy or DURALUMIN are each threaded on to the respective end of the pin 27, and the whole unit 20-29 is tightened into a pack so that the rings 20-25 are statically prestressed such as to give a pressure of about 500 kg/cm$^2$, in order to withstand without this disintegration the heavy accelerations to which they are subjected when the feed voltages from the two-wire cable 4 are put across the lines 30, 31, which are electrically connected to the discs 26 such that one line is connected to alternate discs while the other line is connected to the remaining discs.

The transducer has a length which is half the wave length of the alternating current with which it is fed. The length of the resonator rods 28, 29 are different and are determined by the following relationship:

$$\frac{wl_c}{v_c} + \tan^{-1}\left[\left[\frac{A_1 \cdot P_1 \cdot V_1}{A_c \cdot P_c \cdot V_c}\right] \cdot \tan\left[\frac{wl_1}{v_1}\right]\right] +$$
$$+ \tan^{-1}\left[\left[\frac{A_2 \cdot P_2 \cdot V_2}{A_c \cdot P_c \cdot V_c}\right] \cdot \tan\left[\frac{wl_2}{v_2}\right]\right] = \pi$$

where $$f = \frac{w}{2\pi}$$

and where $l_1$, $l_2$, $l_c$ denotes the length of the rod 2B, 29. the length of the aggregate of the rings 20, 25, respectively; $v_1$, $v_2$, $v_c$ denote the velocity of sound for the same units; $A_1$, $A_2$ $A_c$, denote the cross-sectional area of these units: and $P_1$, $P_2$ $P_c$ denote the density of these units. According to an advantageous embodiment of the invention the relationship $l_1 : l_2 = 2.5$, the transducer then oscillating with a stroke of about 10 $\mu$m at the end surface 32 and with 4 $\mu$m at the end surface 33. The amplitude transformer is connected to the end surface 32 of the transducer and amplifies the magnitude of the stroke by about 30 times.

The transducer and the amplitude transformer are united by means of a bolt which connects the two units together with an ample degree of coupling.

The inventive amplitude transformer has a length in the order of magnitude 0.72 times the wavelength of the ultra sound, and is made in a cohesive piece from a material which is a heat-treated titanium alloy including aluminium and vanadium. The iron content may be at most 0.3% and the hydrogen content at most 0.01%. The amplitude transformer includes three sections 40, 41, 42. Section 40 has a cylindrical form and merges into section 41, the geometry of which is a wave function of the fourth order Fourier form i.e.

$$U(X) = \sum_{n=0}^{n=3} a_k \cdot \cos K \cdot \pi \cdot X$$

where

U(X) = longitudinal deflection in X-direction $a_K$ = constants

The section 42 is substantially tapering. With this embodiment of the knife there is obtained a pronounced resonance related to the longitudinal oscillation movement, and from the frequency aspect, this resonance is greatly separated from secondary longitudinal resonances and remaining resonances related to transverse oscillations. As will be seen from the diagram in FIG. 6, read in conjunction with FIG. 3, where the abscissa relates to the length of the amplitude transformer in respect of curves A and B, and the ordinate relates to the longitudinal oscillation in respect of curve A and the magnitude of material stress in respect of curve B, it will be seen that the stroke of the knife is at a maximum at the outmost tip 43 and decreases towards zero at the point where the bore 6 opens out in the surface. It is thus possible to seal the connection of the suction tube to the bore with O-ring seals, which will when not disintegrate due to vibration. For the same reason, the handle 1 is attached to the transducer 5 at a velocity node, whereby the handle will not vibrate and the surgeon's hand will not be injured by vibrations. Furthermore, it will be seen from the curve B that material stresses are at a maximum, not at the outmost tip 43, but in a region situated a distance L inwards of this tip. The advantage of this geometry of the knife is that its life increases substantially in comparison with known knives.

It is easy experimentally to check where the resonances of the knife are by connecting it to the transducer and feeding the latter with electrical energy at ultrasonic frequency, adjusted to different frequencies. The stroke executed by the outmost tip 43 is measured by a dial gage, and the crests in the curve obtained from these measurements denote the different resonance points of the knife.

FIG. 4 is a block diagram of the power supply and frequency control of the ultrasonic knife. A voltage-controlled oscillator 50 sends a square wave voltage with an ultrasonic frequency to an integrator 51. The frequency range of the voltage-controlled oscillator is adjusted with a dc voltage taken from a voltage divider 52, 53, 54 comprising a frequency adjusting potentiometer 52. By the integrator 51 the square wave voltage is converted into a triangular wave form which is supplied to a power adjustment device 55 where it is compared with a constant, adjustable, dc voltage level taken from a further voltage divider 56, 57, 58 via a power adjustment potentiometer 57. The maximum and the minimum power respectively are set by potentiometers 56, 57. The power adjustment device 55 comprises two voltage comparators 59, 60, embodied by two differential amplifiers, as well as an inverter 61A. The power adjustment device 55 operates in the following manner; with the potentiometer 57 the surgeon sets the desired rate of tissue removal within the extreme values which typically range from about 5 $\mu$m to about 300 $\mu$m. Normally the ultrasonic knife is operated with 50–15 $\mu$m. At a the voltage corresponds to the desired power level. This power level reference voltage is supplied to the inverting input of comparator 59 and via inverter 61A in opposite phase to the inverting input of comparator 60. The triangular wave voltage from integrator 51 is compared with said power level reference voltage. The differential amplifiers will change their output states each time the triangular wave voltage crosses the power level reference voltage. The output signals from comparators 59 and 60 are combined in a pulse width filter 61 from which the combined pulse width modulated signal is supplied to a switched power amplifier 62. Thus, the power amplifier 62 receives a pulse width modulated square wave signal the repetition frequency of which equals that of the triangular voltage wave signal. The width of the pulses, that is the energy contents of the pulses, correspond to the surgeon's demand. The power adjustment is accurate and does not affect the frequency of the ultrasonic power applied to the ultrasonic knife. Short switching times are achieved. Accordingly, power control is performed without varying the supply voltage.

From the power amplifier 61 the amplified square wave signal is fed to a primary winding 63 on a ring core transformer 64, the core of which is earthed. The other end of the primary winding 63 is earthed via a capacitor 65. The power-amplified square wave voltage is transformed up in the ring transformer and is taken out across the secondary winding 66 of the transformer where it is fed via a primary winding 67 of a current transformer 68 to the two-wire cord 4. More specifically, one of the cord wires is connected to one end of the secondary winding 66 and to one plate of a capacitor 69 the other plate of which is connected to one end of the primary winding 67 on the current transformer 68. The other end of this primary winding 67 is connected to the other wire of the two-wire cord and the center tap of the current transformer is connected to the remaining end of the secondary winding 66 on the ring transformer 64. The current transformer 68 has a secondary winding 70, one end of which is earthed and the other end of which is connected to an amplifier 71. The ring transformer 64 also has secondary winding 72, one end of which is earthed and the other end connected to the input of an amplifier 73. It is obvious that the voltage U through the secondary winding 72 is proportional to the square wave voltage fed to the knife, while the current I in the secondary winding 70 is proportional to the magnitude of the current with which the knife is fed. The phase position between the supply voltage current and voltage is detected in a phase detector 74 having on its output a direct voltage proportional to the phase difference. This direct voltage is fed to the control input of the voltage controlled oscillator 50 via a resistor 75. It is suitable to arrange so that the phase angle is zero when the ultrasonic knife has a resonance at the mentioned fundamental frequency. This is arranged by the secondary winding 66 of the transformer being dimensioned such that it satisfies the equation:

$$L^2 = f^2 \cdot \pi^2 \cdot C_o^{-1}$$

where L denotes the inductance in H of the secondary winding 66, f is the frequency of the square wave voltage and Co the capacitance across the ultrasonic knife including the two-wire cord 4. If this equation is satisfied, the ultrasonic knife and its cord behave as a pure ohmic load at the desired resonance frequency.

The capacitor 69 compensates the capacitance of the two-wire cord 4. This cord capacitance is great when the cord is long, and with the aid of the capacitor 69 it is achieved that the cord capacity does not affect the phase angle of the ultrasonic knife. The network with the components 66–69 also has the effect that it provides a phase shift enabling the capacitor 69 to be used as compensator for the capacitance of the two-wire cable 4.

Figure 5:
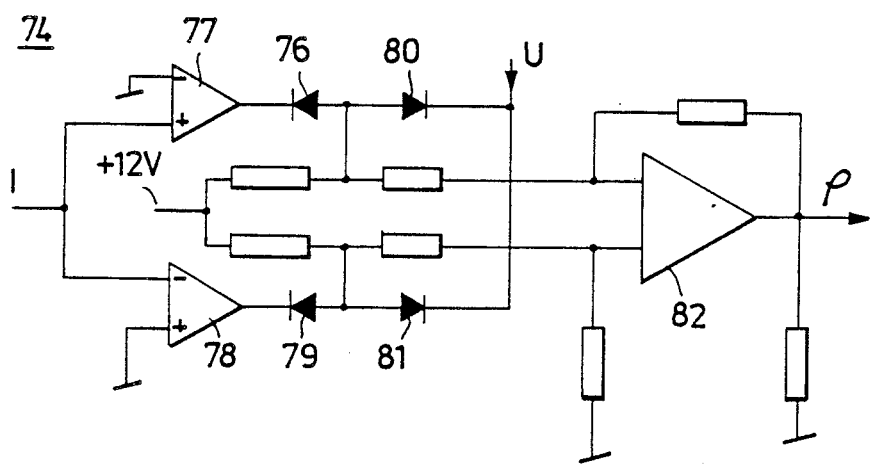
FIG. 5 is a detailed block diagram of the phase comparator illustrated in FIG. 4.

The phase error magnitude is dependent on the degree of filling of the duct 6, i.e. the amount of fragments and liquid in the duct 6, causing the oscillating system to be modified and its resonance frequency to change. It is then necessary for the frequency generator immediately to send a feed voltage with the new resonance frequency, otherwise the knife would stop its removal of tissue material. The error signal from the phase detector 74 adjusts the voltage controlled oscillator 50 to the new resonance frequency of the knife. It is now important that the phase detector does not lock on to a spurious resonance frequency during this regulation process. However, since the knife has a geometry stated, these undesired frequencies are greatly separated from the desired resonance frequency. This means that filters and the like can be excluded from the phase control circuit. A simple detector of the kind illustrated in FIG. 5 may be used instead. The signals U and I are each fed to the respective diagonal branch of the bridge-connected detector 74 which has a diode 76, an amplifier 77, a second amplifier 78 and a diode 79 in one branch and in its other branch a diode 80 and a second diode 81. The voltage between the branches of the bridge is detected by the amplifier 82, sending on its output the mentioned direct current signal, the level of which corresponds to the phase angle between current and voltage for the power fed to the ultrasonic knife.

Apart from the above-mentioned advantage with automatic phase control, the phase lock means that if the operator accidentally drops the knife on the floor, for example, he only need to take a new knife and connect it to the two-wire cord and continue the operation, without having to carry out any calibrations of the electrical equipment. This is an advantage in comparison with the U.S. Pat. No. 4,223,676, where renewed calibration of the frequency control must be carried out if the tip is changed.

The ring transformer secondary winding 66, the current transformer primary winding 67 and the capacitor 69 are built into a housing, schematically indicated by the dashed line 83 in FIG. 4, this housing being mechanically connected to the casing of the frequency generator. The housing 83 serves as a screen and surrounds the circuits which are in galvanic communication with the patient. In this way there is achieved that leakage voltages to the supply and other components can be kept so low that the frequency generator meets the protective standard IEC 601-1, class body floating.

For the clinically tried ultrasonic frequency 24000 Hz an amplitude transformer in accordance with the invention has its desired resonance frequency at 24500 Hz. There is a weak transverse resonance at 20200 Hz and a weak, probably transverse resonance at 30200 Hz. It will thus be understood that with this geometry the undesired spurious resonances are at a frequency range from 17% to 23% from the desired frequency, i.e. abut 20% with reference to the desired resonance frequency.

The resonance frequency for the ultrasonic transformer varies by only about 120 Hz during operation of the ultrasonic aspirator which means that the control input to the voltage controlled oscillator 50 can have the simple implementation illustrated to the left in FIG. 4 and which comprises a voltage divider 52-54, having an output voltage adjustable to the desired voltage level with the aid of a potentiometer 52. This voltage level thus biases the voltage controlled oscillator to the desired resonance frequency.

I claim:

1. In an ultrasonic knife device having a transducer means for converting electrical energy at an ultrasonic frequency to mechanical oscillations, an amplitude transformer means mechanically connected to the transducer means for amplifying the stroke of mechanical oscillation, wherein said amplitude transformer means is an elongated integral unit having a substantially cylindrical portion connected to the transducer neons an intermediate portion adjacent to the cylindrical portion, a tip portion adjacent to the intermediate portion, and a through bore passing through the intermediate portion and the tip portion for aspirating tissue, the improvement wherein the length of the amplitude transformer means is 0.72 times the wavelength of the ultrasonic frequency, and wherein the intermediate portion has geometric form which is the curve of a wave function of the fourth order Fourier form and the tip portion is conical, whereby the maximum stroke of the longitudinal oscillation mode is at a predetermined resonant frequency, this resonant frequency being separated, in order of magnitude of 20% from the harmonics of the predetermined resonant frequency in the longitudinal oscillation mode, and resonant frequencies of oscillations in the transverse mode.

2. An ultrasonic knife device as claimed in claim 1, wherein the amplitude transformer neons is made from a heat-treated alloy of titanium, aluminium, vanadium and iron with a hydrogen content of less than 0.3% and an oxygen content of less than 0.01%.

3. An ultrasonic knife device as set forth in claim 1 having a voltage controlled oscillator, a power amplifier connected to the oscillator and a control loop coupled to said voltage controlled oscillator for frequency control of the oscillator in response to the magnitude of a phase error between the current and voltage of the energy the power amplifier feeds to the ultrasonic knife, wherein the control loop includes a ring core transformer with primary and secondary windings for the feed energy, a winding arranged on the ring transformer for sensing the voltage of the feed energy, a current transformer coupled to the ring transformer for sensing the current of the feed energy and a phase comparator coupled to the ring transformer and the current transformer for sensing the phase difference between the current and voltage and for feeding a direct voltage signal corresponding thereto the to the control input of the oscillator.

4. An ultrasonic knife device as claimed in claim 3, including a compensation capacitor and a two wire cord wherein the current transformer has a primary winding provided with a central tap, with said tap connected to one end of the secondary winding of the ring core transformer, one end of the primary winding being connected to one plate of the compensation capacitor and the other end of the primary winding being connected to one wire of the two-wire cord connecting the ultrasonic knife to the frequency generator, the second plate of the compensation capacitor being connected to the other wire of the core, the other wire being connected to the other end of the ring transformer secondary winding.

5. An ultrasonic knife device as claimed in claim 4, wherein the capacitance of the compensation capacitor is selected such that it compensates for the capacity of the two wire cord.

6. An ultrasonic knife device as claimed in claim 4, wherein the secondary winding of the ring core transformer is dimensioned to satisfy the equation:

$$L^2 = f^2 \cdot \pi^2 \cdot C_O^{-1}$$

L = inductance (H) of the secondary winding
f = feed energy frequency (Hz)
$C_O$ = capacitance of ultrasonic knife,
the phase difference between current and voltage being zero degrees at the desired resonant frequency.

7. An ultrasonic knife device as claimed in claim 4, including a housing and a frequency generator chassis wherein the secondary winding of the ring core transformer, the primary winding of the current transformer and the compensation capacitor are positioned in the housing which is mechanically attached to the frequency generator chassis.

* * * * *